United States Patent
Shashidhar et al.

(10) Patent No.: US 9,891,187 B1
(45) Date of Patent: Feb. 13, 2018

(54) SYSTEMS AND METHODS FOR ION MEASUREMENTS

(71) Applicants: Ranganathan Shashidhar, Needham Heights, MA (US); Yufeng Ma, Needham Heights, MA (US); James A. Kane, Needham Heights, MA (US)

(72) Inventors: Ranganathan Shashidhar, Needham Heights, MA (US); Yufeng Ma, Needham Heights, MA (US); James A. Kane, Needham Heights, MA (US)

(73) Assignee: POLESTAR TECHNOLOGIES, INC., Needham Heights, MA (US)

( * ) Notice: Subject to any disclaimer, the term of this patent is extended or adjusted under 35 U.S.C. 154(b) by 7 days.

(21) Appl. No.: 14/681,257

(22) Filed: Apr. 8, 2015

Related U.S. Application Data

(60) Provisional application No. 61/976,830, filed on Apr. 8, 2014.

(51) Int. Cl.
*G01N 27/333* (2006.01)
*G01N 27/42* (2006.01)

(52) U.S. Cl.
CPC ....... *G01N 27/3335* (2013.01); *G01N 27/423* (2013.01)

(58) Field of Classification Search
CPC .. G01N 27/3335; G01N 27/423; G01N 27/49; G01N 27/333; C01B 31/022; C01B 2202/00; B82Y 30/00
See application file for complete search history.

(56) References Cited

U.S. PATENT DOCUMENTS

| | | | |
|---|---|---|---|
| 2009/0278556 A1* | 11/2009 | Man | G01N 27/4146 324/693 |
| 2010/0068406 A1* | 3/2010 | Man | B05D 1/60 427/469 |
| 2011/0163296 A1* | 7/2011 | Pace | B82Y 15/00 257/24 |

(Continued)

OTHER PUBLICATIONS

Bertini et al., Bioinorganic Chemistry, Chapter 3: Calcium in Biological Systems, Section III., Subsection A, Copyright 1994.*

(Continued)

*Primary Examiner* — Susan D Leong
*Assistant Examiner* — Joshua L Allen
(74) *Attorney, Agent, or Firm* — Burns & Levinson LLP; Orlando Lopez

(57) ABSTRACT

Systems that can measure small changes in ion concentrations and method of manufacturing and using those systems. The system includes a substrate, a plurality of multi-walled carbon nanotubes, each multi-walled carbon nanotube from the plurality of multi-walled carbon nanotubes having two ends and a surface extending between the two ends, one of the two ends being disposed on and operatively attached to the substrate, the other of the two ends not being disposed on the substrate, a number of organic molecules; each organic molecule bound to one multi-walled carbon nanotube, each organic molecule also having an end group with affinity for a predetermined ion(s), and a substantially nonconducting polymer deposited on a portion of each multi-walled carbon nanotube, the portion substantially not including locations on each multiwalled carbon nanotube at which each organic molecule is chelated.

19 Claims, 14 Drawing Sheets

(56) References Cited

U.S. PATENT DOCUMENTS

2012/0125771 A1* 5/2012 Salzer .................. G01N 27/308
  204/412

OTHER PUBLICATIONS

BASi, Chronoamperometry/chronocoulometry, Bioanalytical Systems, Inc., p. 1-5.*

Telford et al., Detection of Plasma Membrane Ca2+-ATPase Activity in Mouse T Lymphocytes by Flow Cytometry Using Fluo-3-Loaded Vesicles, Cytometry 24 (1996) 243-250.*

Johnson et al., Molecular Probes Handbook 11th Edition (2010), Chapter 19, Indicators for Ca2+, Mg2+, Zn2+, and Other Metal Ions, Invitrogen—A Thermo Fisher Scientific Company.*

Zanarini et al., Facile functionalization by π-stacking of macroscopic substrates made of vertically aligned carbon nanotubes: tracking reactive groups by electrochemiluminescence, Electrochimica Acta, 56 (2011) 9269-9276.*

Trapani et al., Intracellular magnesium detection: imaging a brighter future, Analyst 135 (2010) 1855-1866.*

Fukushi et al., Determination of magnesium and calcium ions in seawater by capillary zone electrophoresis, Fresenius J. Anal. Chem., 356 (1996) 150-154.*

Grand et al., Determination of dissolved zinc in seawater using micro-sequential injection lab-on-valve with fluorescent detection, Analyst, 136 (2011) 2747-2755.*

Flavel et al., Electrochemical detection of copper using Gly-Gly-His modified carbon nanotube biosensor, Silicon, 3 (20110 163-171.*

Mittal et al., Carbon Nanotubes Surface Modifications: An Overview, Surface Modifications of Nantube Fillers, First Edition, Wiley-VCH Verlag GmbH & Co., 2011, p. 1-24.*

Yuqing et al., Using electropolymerized non-conducting polymers to develop enzyme amperometric biosensors, Trends in Biotechnology, 22(5) (2004) 227-231.*

Cai et al., "A molecular-imprint nanosensor for ultrasensitive detection of proteins", Nature Nanotechnology, vol. 5, Aug. 2010, 597-601.

Zhong et al., "Detection of femtomolar level osteosarcoma-related gene via a chronocoulometric DNA biosensor based on nanostructure gold electrode", International Journal of Nanomedicine 2012:7, 527-536.

Vaartnou et al., "Impedance study of chloride ions adsorption on Bi(111) and Bi(011) single crystal planes in ethanol", Journal of Electroanalytical Chemistry 578 (2005), 273-282.

Orr et al., "Anthropogenic ocean acidification over the twenty-first century and its impact on calcifying organisms", Nature, vol. 437, Sep. 2005, 681-686.

Nimick et al., "Diel biogeochemical processes and their effect on the aqueous chemistry of streams: A review", Chemical Geology 283 (2011), 3-17.

* cited by examiner

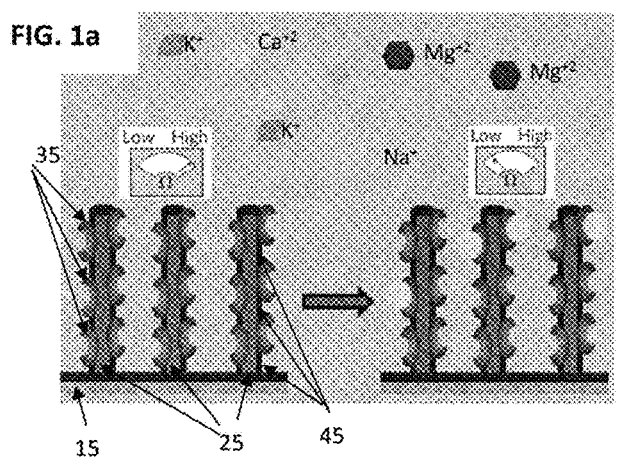
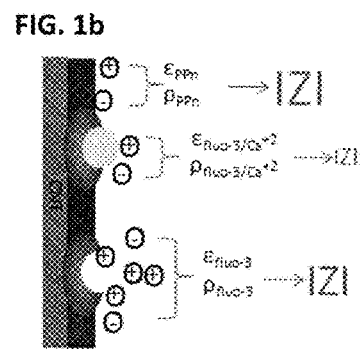
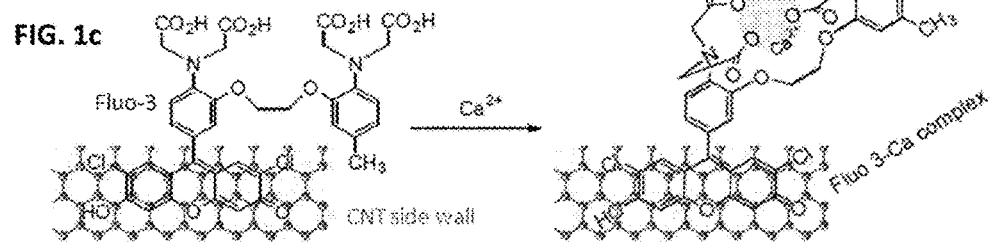

SYSTEMS AND METHODS FOR ION MEASUREMENTS

STATEMENT REGARDING FEDERALLY SPONSORED RESEARCH OR DEVELOPMENT

This invention was made partially with U.S. Government support from the NOAA under contract number WC-133R-12-CN-0070. The U.S. Government has certain rights in the invention.

CROSS-REFERENCE TO RELATED APPLICATIONS

This application claims priority to U.S. Provisional Application No. 61/976,830, filed Apr. 8, 2014, entitled SYSTEMS AND METHODS FOR CALCIUM ION MEASUREMENTS, the entire contents which are incorporated herein by reference and for all purposes.

BACKGROUND

These teachings relate generally to ion measurements.

In one exemplary embodiment, these teachings can be applied to measurement of small changes in calcification.

There is a need for measurement of small changes in calcification. For example, with ever-increasing amounts of carbon dioxide ($CO_2$) entering the atmosphere, oceans are absorbing more and more $CO_2$. Part of this $CO_2$ becomes carbonic acid which dissolves in oceans, lowering pH levels. This phenomenon is known as ocean acidification which lowers the carbonate saturation states. A consequence of this phenomenon is that marine calcifying organisms, like corals, coralline algae, molluscs and foraminifera, have difficulties producing their skeletons and shells at current rates, with potentially severe implications for marine ecosystems, including coral reefs. In fact, there has been a recent research study by the U.S. Geological Survey on the effects of ocean acidification on crustose coralline algae (a cosmopolitan group of calcifying algae that is ecologically important in most shallow-water habitats). It was found that the recruitment rate and growth of crustose coralline algae were severely inhibited in the elevated carbon dioxide mesocosms. The calcification rates in reef-building corals may have slowed down by 10% over the last 150 year, with predictions to slow another 15-30% by the end of the century.

As can be seen from the table below, none of the existing methods for measuring calcification rates-measurement of total alkalinity and extraction of the calcification rate using equations based on certain assumptions, direct measurements of $Ca^{+2}$ with an ion selective electrode and complexometric titration, are suitable and cannot meet the requirements for the needed calcium ion measurements.

There is a need for systems that can measure small changes in calcification (calcium ion measurements).

There is also a need for systems that can measure small changes in calcification in the presence of other interfering ions.

In other exemplary embodiments, there is a need for measurement of ions in applications including environmental monitoring as well as biological fields. These applications include detection of other ions such as magnesium, zinc, cadmium, copper, nickel, iron, arsenic, mercury, antimony, gold and other metal ions, including heavy metal ions, transition-metal ions and main-group ions.

TABLE 1

Comparison of recent advances in detection of $Ca^{+2}$

| Detection methods | Advantages | Disadvantages |
|---|---|---|
| Field effect transistor (FET) based on Carbon nanotube (CNT)/probe composites | Ultra sensitive (<1 nM) Good selectivity | Limited dynamic range Small relative change in current at high concentrations |
| Fluorescent fiber-optic sensor based on dye probe | Good sensitivity (~40 nM) Rapid response (<1 second) Good selectivity | Small dynamic range (<0.1 mM) Complex measurement |
| Microchip-based fiber optic (UV) detection technique | Great selectivity | Does not have high sensitivity Low dynamic range |
| Electrochemical sensor based on silicon nanowires modified with phosphotyrosine | Good sensitivity Rapid response | Low dynamic range |
| Microcantilevers modified with ion-selective self-assembled monolayers (SAMs) | High sensitivity Good selectivity | Very low dynamic range Very sensitive to mechanical disturbances |

BRIEF SUMMARY

Systems for performing measurements of predetermined ions and method of manufacturing and using those systems are disclosed herein below.

In one or more embodiments, the system of these teachings includes a substrate, a plurality of multi-walled carbon nanotubes, each multi-walled carbon nanotube from the plurality of multi-walled carbon nanotubes having two ends and a surface extending between the two ends, one of the two ends being disposed on and operatively attached to the substrate, the other of the two ends not being disposed on the substrate, a number of organic molecules, each organic molecule bound to one multi-walled carbon nanotube and having an end group configured to chelate a predetermined ion, and a substantially nonconducting polymer deposited on a portion of each multiwalled carbon nanotube, the portion substantially not including locations on each multiwalled carbon nanotube at which an organic molecule is bound, predetermined ion measurements being performed, after the predetermined ion is chelated, by one of coulometric measurements or amperometric measurements.

In one or more embodiments, the method for fabricating the sensor of these teachings includes binding at least one organic molecule to at least one multiwalled carbon nanotube from an array of multi-walled carbon nanotubes, one end of each one multiwalled carbon nanotube being disposed on and attached to a substrate, each organic molecule having an end group configured to chelate a predetermined ion and coating a portion of each multiwalled carbon nanotube with a substantially nonconducting polymer, the portion substantially not including locations on each multiwalled carbon nanotube at which at least one organic molecule is bound.

A number of other embodiments also are disclosed.

For a better understanding of the present teachings, together with other and further objects thereof, reference is made to the accompanying drawings and detailed description and its scope will be pointed out in the appended claims.

BRIEF DESCRIPTION OF THE DRAWINGS

FIGS. 1a-1c show one embodiment of the sensor of these teachings;

DETAILED DESCRIPTION

Figure 2:
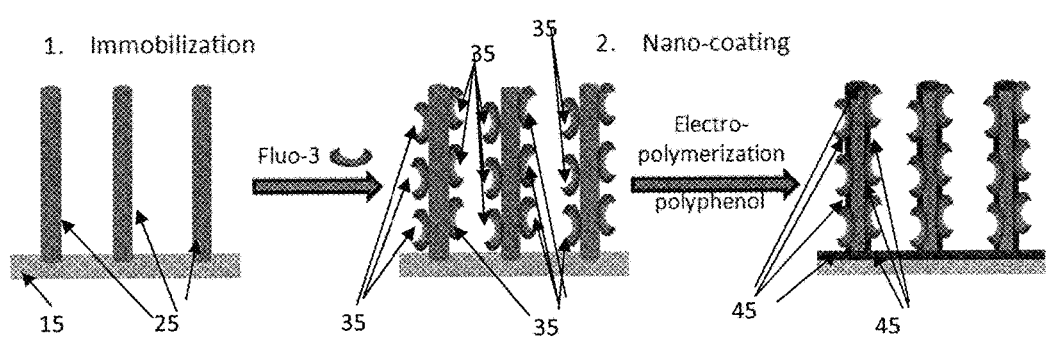
FIG. 2 shows one embodiment of the method of fabricating the sensor of these teachings.

The following detailed description presents the currently contemplated modes of carrying out the invention. The description is not to be taken in a limiting sense, but is made merely for the purpose of illustrating the general principles of the invention, since the scope of the invention is best defined by the appended claims.

As used herein, the singular forms "a," "an," and "the" include the plural reference unless the context clearly dictates otherwise.

Except where otherwise indicated, all numbers expressing quantities of ingredients, reaction conditions, and so forth used in the specification and claims are to be understood as being modified in all instances by the term "about."

In one or more embodiments, the system of these teachings includes a substrate, a plurality of multi-walled carbon nanotubes, each multi-walled carbon nanotube from the plurality of multi-walled carbon nanotubes having two ends and a surface extending between the two ends, one of the two ends being disposed on and operatively attached to the substrate, the other of the two ends not being disposed on the substrate, a number of organic molecules, each organic molecule bound to one multi-walled carbon nanotube and having an end group configured to chelate a predetermined ion, and a substantially nonconducting polymer deposited on a portion of each multiwalled carbon nanotube, the portion substantially not including locations on each multiwalled carbon nanotube at which an organic molecule is bound, predetermined ion measurements being performed, after the predetermined ion is chelated, by one of coulometric measurements or amperometric measurements.

Amperometric measurements, as used herein, are measurements of current, including impedance measurements.

In one instance, the predetermined ion is a calcium ion ($Ca^{2+}$); and where in the end group is configured to chelate the calcium ion ($Ca^{2+}$).

An exemplary embodiment of a system for measurement of calcium ions is presented herein below. It should be noted that these teachings are not limited only to the exemplary embodiment.

The organic molecules, in that instance, are labeled calcium indicators molecules that exhibit an increase in fluorescence upon binding $Ca^{2+}$. In one instance, the labeled calcium indicator is Fluo-3 ($C_{51}H_{50}Cl_2N_2O_{23}$-{2-(2-{2-Bis(carboxymethy)amino-5-(2,7-dichloro-6-hydroxy-3-oxo-3H-xanthen-9-yl)phenoxy}ethoxy)-4-methylphenyl(carboxymethyl)amino }acetic acid). In other instances, the labeled calcium indicator is Fluo-4 (AM or NW), an analog of fluo-3 with the two chlorine substituents replaced by fluorines. This structural modification results in increased fluorescence excitation at 488 nm. Other instances of labeled calcium indicator are Fluo-5F, fluo-5N, and fluo-4FF, which are analogs of fluo-4 with lower $Ca^{+2}$ binding affinity.

In one instance, the substrate is, for example, but not limited to, metal, glass, silicon, etc. In one embodiment, the substrate is first coated with an adhesion layer (for example, titanium or chromium), and then overcoated with nanoparticles (in one instance, nickel nanoparticles), then introduced to a vacuum deposition chamber. The deposition of the nanoparticles defines the sites of the multiwalled carbon nanotubes (MCNT). In one instance, the packing density of the multiwalled carbon nanotubes (MCNTs) is at least $10^9$ MCNTs/cm$^2$.

In one instance, the substantially nonconducting polymer is a polymer from the polyphenol class and the thickness of the coating on the portion of each multiwalled carbon nanotube is in the nano-meter range.

In one embodiment, the sensor of these teachings meets the following requirements:

Ability to measure $Ca^{+2}$ to a precision of ±5 µM

Ability to measure small changes in concentration in presence of high background concentrations (10 mM) of $Ca^{+2}$ Ability to measure without interference from other ions like magnesium ($Mg^{+2}$) present in sea water Capability to measure the small change (50 µM) of $Ca^{+2}$ ions in a short period of a 24-hour 'diel cycle'.

The above requirements require a sensor that is capable of distinguishing and quantifying the change of $Ca^{+2}$ at 50 µM level with a precision of ±5 µM in seawater that contains 10.2 mM of $Ca^{+2}$. This implies that the dynamic range of the developed sensor should cover from a low concentration of <5 µM to a high concentration of >10.25 mM, i.e. over a range of $10^3$. Table 1 shows that recent advances in calcium detection do not meet the above requirements.

The following specifies what is required for a design of a practical sensor that meets the above described requirements. Assuming that the calcium ions interact with binding sites in a sensing matrix following the Langmuir isotherm, the number of binding sites ($N_b$) with calcium ions can be described as:

$$N_b = N_t \cdot Ca^{+2}/(K_{ds} + Ca^{+2}),$$

where $N_t$, $Ca^{+2}$, and $K_{ds}$ represent the total number of binding sites, the concentration of calcium ions in bulk solution, and the dissociation constant between binding sites and calcium ions, respectively. A dissociation constant value $K_{ds}$ of 22 µM has been reported for the binding between calcium ions and Fluo-4-AM sensing molecules. With the use of this value, we estimated the corresponding change in the number of binding sites (Fluo-4-AM sensing molecules) ($\Delta N_b$) when the calcium ion concentration changes from 10.25 mM to 10.20 mM (Change in 50 µM) during the 24-hour 'diel cycles' due to calcification. The relationship between signal change ($\Delta_{signal}$) and the total number of binding sites (Fluo-4-AM) is given by:

$$\Delta_{signal} = \eta \cdot \Delta N_b = \eta \cdot 1.05 \times 10^{-6} \cdot N_t = 1.05 \times 10^{-6} \cdot N_{effective}$$

Here η is a modifying parameter and $N_{effective}$ is the total number of effective binding sites. Normally, a detectable signal change ($\Delta_{signal}$) has to be 3 times higher than the noise level of the detection method ($P_{method}$). Therefore, the relationship can be illustrated as:

$$N_{effective} \geq P_{method}/(3.5 \times 10^{-7}),$$

Whereas, $P_{method}$ is the precision or accuracy for applied detection method itself. The noise level observed in CHI 720C workstation is at $10^{-12}$ level. Hence, the minimum chelating units are required to be as large as $3 \times 10^{-6}$ mole.

For a CNT arrayed electrode with 100 times enhanced surface area, the chelating units (fluo-3 or fluo-4) is calculated to be as high as $1.5 \times 10^{-4}$ mole per centimeter square.

Embodiments of the sensor of these teachings meet this requirement.

In order to further elucidate these teachings, an exemplary embodiment is disclosed herein below.

FIGS. 1a-1c show the Detection mechanism in the exemplary embodiment of these teachings. FIG. 1a shows the sensor impedance responses at critical stages of detection. The MCNT 25 surface with the labeled calcium indicators 35 bound to the MCNT surface is coated with nonconducting polyphenol 45. (The MCNT array 25 is grown on a substrate 15.) FIG. 1b shows three scenarios of sensor surface conditions closely related to resistivity ($\rho$) and permittivity ($\epsilon$): (i) MCNT surface coated with PPn, ($\epsilon_{PPn}$, $\rho_{PPn}$); (ii) Calcium chelator binds with calcium ion ($\epsilon_{fluo-3/Ca+2}$, $\rho_{fluo-3/Ca+2}$); (iii) un-occupied chelator ($\epsilon_{fluo-3}$, $\rho_{fluo-3}$). The differently sized |Z| reflects the relative values of impedance. FIG. 1c shows a binding event representation.

An organic calcium ion chelating molecule is selected as a capturing site for binding the calcium ion. This calcium ion-specific polyamino carboxylic acid (FIG. 1c) and its derivatives have been used for the selective detection of intracellular calcium ions where the complexity and interference are much greater than seawater. The remarkable specificity of fluo-3 originates from its chelating site that resembles BAPTA (1,2bis(o-aminophenoxy)ethane-N,N,N', N'-tetraacetic), which is a calcium-specific polyamine carboxylic acid. For instance, it has a much higher affinity for $Ca^{+2}$ than for the main interfering ion ($Mg^{+2}$) in which $\log(K_{Ca}/K_{Mg})=5.2$. Importantly, fluo-3 possesses pKa between 5.4 and 6.4, and will be not protonated in seawater. This property indicates that the deprotonation step is not included in its calcium complexation step, thereby leading to even faster binding events without the involvement of proton. Also, a non-conducting polymer (polyphenol) nanolayer is coated onto the sensor architecture to suppress the non-specific response caused by the contact between exposed conductive electrode surface with other ions.

Efficient transduction which converts binding events into a detectable signal is necessary in the sensor design. In embodiments of the sensor of these teachings, the strong $\pi$-$\pi$ stacking interaction between the big planar aromatic structure of fluo-3 and graphitic sidewall of carbon nanotube (as shown in FIG. 1c), which can tightly anchor them together, is advantageously used. This effective interaction will rapidly and sensitively transduct the binding events onto electrode through the superior conductive MCNT.

Because fluorophores can quench or photo-bleach, conventional optical methods are not applicable to monitor small changes in presence of high concentrations of target analytes. Nevertheless, electrochemical techniques appear to be well-suited for detecting the binding-induced changes. The sensitivity of the electrochemical detection methods has been demonstrated in DNA hybridization (femto-molar) and protein (pico-gram per liter) detections. Another advantage of the electrochemical detection method is the promise of rapid and inexpensive screening in platforms characterized by low power, mass and volume requirements. Chronocoulometric method, which involves monitoring changes in charge as a function of time, is used to detect the binding event.

The components for assembling the above-described embodiment of the sensor of these teachings are all electrochemically inert. Therefore, the change of permittivity $\epsilon$ and resistivity $\rho$ in the surface materials in response to calcium ion binding (FIG. 1b) can be considered as the primary mechanism of signaling (chelated calcium ions induce higher $\epsilon$ and lower $\rho$ than the replaced water in the empty binding sites, leading to increased capacitance and decreased resistance). This change in electrochemical signal is directly proportional to the amount of calcium ions caught by chelating molecules. In addition, it has been shown that derivatives of fluo-3 probe can reversibly bind to calcium ions. This property may bring another advantage (reusability) for the sensing technology of these teachings.

In another instance, the predetermined ion is a magnesium ion ($Mg^{2+}$) and the end group of an organic molecule is configured to chelate the magnesium ion ($Mg^{2+}$). For $Mg^{2+}$, one embodiment of the organic molecule indicator is Mag-Fluo-4 ($C_{25}H_{13}F_2K_4NO_{10}$). Indicators for $Mg^2$, $Zn^{2+}$ and Other Metal Ions can be found in The Molecular Probes® Handbook, Chapter 19, Indicators for Ca2+, Mg2+, Zn2+ and Other Metal Ions, (2010), which is incorporated by reference herein in its entirety and for all purposes. Mag-fluo-4 is an analog of fluo-4.

In still another instance, the predetermined ion is a Zinc ion ($Zn^{2+}$) and the end group of an organic molecule is configured to chelate the Zinc ion ($Zn^{2+}$). One embodiment of the organic molecule indicator for a Zinc ion ($Zn^{2+}$) is $C_{34}H_{24}F_2K_4N_2O_{12}$-N-(carboxymethyl)-N-[4-(2,7-difluoro-6-hydroxy-3-oxo-3H-xanthen-9-yl)-2-methoxyphenyl].

For organic molecule indicators that are similar to or analogs of fluo-3 and fluo-4, the behavior, in terms of binding to the multiwall carbon nanotube and to detection of the predetermined ion, can be similar to that found for fluo-3 for measurement of calcium ions.

In a further instance, the predetermined ion is a copper ion ($Cu^{2+}$); and wherein the end group of an organic molecule is configured to chelate the copper ion ($Cu^{2+}$). In one embodiment, for copper ions ($Cu^{2+}$), the organic molecule indicator is glycyl-glycyl-histidine ($C_{10}H_{15}N_5O_4$). In another embodiment, for copper ions ($Cu^{2+}$), the organic molecule indicator is (3,5-dimethyl-1H-pyrazole-1-yl)methylamino acetic acid in conjunction with a large aromatic group, such as, but not limited to pyrene ($C_{16}H_{10}$) or coronene ($C_{24}H_{12}$).

In yet another instance, the predetermined ion(s) is/are one or more of a copper ion ($Cu^+$ or $Cu^{2+}$) or a nickel ion ($Ni^{2+}$ or $Ni^{3+}$); and wherein the end group of an organic molecule is configured to chelate the one or more of the copper ion ($Cu^+$ or $Cu^{2+}$) or the nickel ion ($Ni^{2+}$ or $Ni^{3+}$). In one embodiment, for one or more of a copper ion ($Cu^+$ or $Cu^{2+}$) or a nickel ion ($Ni^{2+}$ or $Ni^{3+}$), the organic molecule indicator includes one or two ethylenediamine ligands ($C_2H_4(NH_2)_2$).

In still another instance, the predetermined ion is an iron ion ($Fe^{2+}$ or $Fe^{3+}$); and wherein the end group of an organic molecule is configured to chelate the iron ion ($Fe^{2+}$ or $Fe^{3+}$). In one embodiment, for iron ions ($Fe^{2+}$ or $Fe^{3+}$), the organic molecule indicator is porphine ($C_{20}H_{14}N_4$).

In another instance, the predetermined ion(s) is/are one or more of a transition-metal ion or a main-group ion; and wherein the end group of an organic molecule is configured to chelate the one or more transition-metal ion or main-group ion. Transition-metal ions and main-group ions include, but are not limited to, manganese ($Mn^{2+}$), copper ($Cu^{2+}$), iron ($Fe^{3+}$) lead ($Pb^{2+}$) or cobalt ($Co^{3+}$). In one embodiment, for one or more of a transition-metal ion or a main-group ion, the organic molecule indicator is ethylenediaminetetraacetic acid ($C_{10}H_{16}N_2O_8$; EDTA).

In yet another instance, the predetermined ion(s) is/are one or more of a heavy metal ion; and wherein the end group of an organic molecule is configured to chelate the one or more of the heavy metal ion. Heavy metal ions include, but are not limited to, arsenic ($As^{3+}$ or $As^{5+}$), mercury ($Hg^{2+}$ or $Hg_2^{2+}$), antimony ($Sb^{3+}$ or $Sb^{5+}$) or gold ($Au^+$ or $Au^{3+}$). In one embodiment, for one or more of a heavy metal ion, the organic indicator is dimercaprol (2,3-dimercapto-1-propanol).

In some instances described above, the organic molecule is bound to the multi-walled carbon nanotubes by π-π stacking between the graphitic surface of the sidewall and planar aromatic structures of the organic molecule. Alternative, in some instances described above, the organic molecule is bound to the multi-walled carbon nanotubes by amide bonds.

In one or more embodiments, the method for fabricating the sensor of these teachings includes immersing a plurality of multi-walled carbon nanotubes in an organic molecule solution for a predetermined time, each multi walled carbon nanotube from the plurality of carbon nanotubes grown on a substrate; immersion resulting in organic molecules being bound to at least one multi-walled carbon nanotube, each organic molecule having an end group configured to chelate a predetermined ion one end of each one multiwalled carbon nanotube being disposed on and attached to a substrate, each organic molecule having an end group configured to being chelated a predetermined ion and coating a portion of each multiwalled carbon nanotube with a substantially nonconducting polymer, the portion substantially not including locations on each multiwalled carbon nanotube at which at least one organic molecule is bound.

The method can also include rinsing, after immersing, the plurality of multi walled carbon nano tubes. In some embodiments, the deposited layer of the substantially nonconducting polymer has a thickness of less than 10 nm.

In one instance, in the method of these teachings, the predetermined ion is a calcium ion ($Ca^{2+}$). In one embodiment of that instance, organic molecule is Fluo-3 ($C_{51}H_{50}Cl_2N_2O_{23}$-([2-(2-{2-[Bis(carboxymethyl)amino]-5-(2,7-dichloro-6-hydroxy-3-oxo-3H-xanthen-9-yl) phenoxy}ethoxy)-4-methylphenyl](carboxymethyl) amino}acetic acid).

An exemplary embodiment of the method of these teachings is presented herein below. It should be noted that these teachings are not limited only to that exemplary embodiment.

One exemplary embodiment of the method of these teachings for sensor fabrication is illustrated in FIG. 2. The embodiment shown in FIG. 2 includes two steps: 1) Immobilization. MWCNT array 25 with a packing density of ~$10^9$ CNTs/$cm^2$ was incubated in a fluo-3 solution (2 mg of fluo-3 in 1 ml of PBS) for 2 hours. The calcium ion chelating molecules 35 (fluo-3) are expected to be strongly bound to the CNT arrayed electrode by π-π stacking between the graphitic surface of CNT sidewall and the planar aromatic structures of fluo-3. After that, the MWCNT array was rinsed with phosphate buffer solution (PBS) to remove the loosely attached fluo-3 molecules; and 2) Nano-coating. Polyphenol (PPn) film 45 was then deposited on the exposed electrode by cyclic voltammetry (CV) in PBS containing 1.5 mM phenol. By using a electrochemical analyzer (for example, CH Instruments 720C), the MWCNT array was subjected to repeated potential scanning, at a rate of 50 mV per second between 0.0 to 0.9 V with respect to the reference electrode (silver wire) for three cycles. This deposition step is self-limiting and can yield a highly conformal coating with a controlled thickness at nano-meter level (Nature Nanotechnology 5, 597 (2010), incorporated herein by reference in its entirety and for all purposes).

In another instance, in the method of these teachings, the predetermined ion is a magnesium ion ($Mg^{2+}$). In one embodiment of that instance, the organic molecule indicator is Mag-Fluo-4 ($C_{25}H_{13}F_2K_4NO_{10}$).

In a further instance, in the method of these teachings, the predetermined ion is a Zinc ion ($Zn^{2+}$). In one embodiment of that instance, the organic molecule is $C_{34}H_{24}F_2K_4N_2O_{12+}$ N-(carboxymethyl)-N-[4-(2,7-difluoro-6hydroxy-3-oxo-3H-xanthen-9-yl)-2-methoxyphenyl].

In yet another instance, in the method of these teachings, predetermined ion is a copper ion ($Cu^{2+}$). In one embodiment of that instance, the organic molecule is glycyl-glycyl-histidine ($C_{10}H_{15}N_5O_4$).

In a further instance, in the method of these teachings, the predetermined ion is a copper ion ($Cu^{2+}$); and wherein the end group of an organic molecule is configured to chelate the copper ion ($Cu^{2+}$). In one embodiment, for copper ions ($Cu^{2+}$), the organic molecule indicator is glycyl-glycyl-histidine ($C_{10}H_{15}N_5O_4$). In another embodiment, for copper ions ($Cu^{2+}$), the organic molecule indicator is (3,5-dimethyl-1H-pyrazole-1-yl)methylamino acetic acid in conjunction with a large aromatic group, such as, but not limited to pyrene ($C_{16}H_{10}$) or coronene ($C_{24}H_{12}$).

In yet another instance, in the method of these teachings, the predetermined ion(s) is/are one or more of a copper ion ($Cu^+$ or $Cu^{2+}$) or a nickel ion ($Ni^{2+}$ or $Ni^{3+}$); and wherein the end group of an organic molecule is configured to chelate the one or more of the copper ion ($Cu^+$ or $Cu^{2+}$) or the nickel ion ($Ni^{2+}$ or $Ni^{3+}$). In one embodiment, for one or more of a copper ion ($Cu^{30}$ or $Cu^{2+}$) or a nickel ion ($Ni^{2+}$ or $Ni^{3+}$), the organic molecule indicator includes one or two ethylenediamine ligands ($C_2H_4(NH_2)_2$).

In still another instance, in the method of these teachings, the predetermined ion is an iron ion ($Fe^{2+}$ or $Fe^{3+}$); and wherein the end group of an organic molecule is configured to chelate the iron ion ($Fe^{2+}$ or $Fe^{3+}$). In one embodiment, for iron ions ($Fe^{2+}$ or $Fe^{3+}$), the organic molecule indicator is porphine ($C_{20}H_{14}N_4$).

In another instance, in the method of these teachings, the predetermined ion(s) is/are one or more of a transition-metal ion or a main-group ion; and wherein the end group of an organic molecule is configured to chelate the one or more transition-metal ion or main-group ion. Transition-metal ions and main-group ions include, but are not limited to, manganese ($Mn^{2+}$), copper ($Cu^{2+}$), iron ($Fe^{3+}$) lead ($Pb^{2+}$) or cobalt ($Co^{3+}$). In one embodiment, for one or more of a transition-metal ion or a main-group ion, the organic molecule indicator is ethylenediaminetetraacetic acid ($C_{10}H_{16}N_2O_8$; EDTA).

In yet another instance, in the method of these teachings, the predetermined ion(s) is/are one or more of a heavy metal ion; and wherein the end group of an organic molecule is configured to chelate the one or more of the heavy metal ion. Heavy metal ions include, but are not limited to, arsenic ($As^{3+}$ or $As^{5+}$), mercury ($Hg^{2+}$ or $Hg_2^{2+}$), antimony ($Sb^{3+}$ or $Sb^{5+}$) or gold ($Au^+$ or $Au^{3+}$). In one embodiment, for one or more of a heavy metal ion, the organic indicator is dimercaprol (2,3-dimercapto-1-propanol).

In some instances described above, the organic molecule is bound to the multi-walled carbon nanotubes by π-π stacking between the graphitic surface of the sidewall and planar aromatic structures of the organic molecule. Alternative, in some instances described above, the organic molecule is bound to the multi-walled carbon nanotubes by amide bonds.

Results obtained using exemplary embodiments, for calcium ions, of the sensor of these teachings are disclosed herein below. The following components were used in fabricating the exemplary embodiments. Phenol chemical was purchased from Sigma-Aldrich and the fluo-3 chelating molecule was purchased from Biotium. They were used as received without any further purification. MWCNT arrays were purchased from Nanolab Inc. Phosphate buffer solution (PBS, 0.1 M, pH 7.4) was made up from $NaH_2PO_4$ and NaOH. Solutions of fluo-3 and phenol were prepared using PBS immediately before each sensor fabrication. All precursor solutions were prepared using de-ionized water (In-line Water Deionizers, Thermo Scientific).

Since the results presented herein below refer to synthetic seawater and natural seawater, the following explanation is presented for completeness. It is known that ions of $Na^+$, $K^+$, $Mg^{2+}$ and $Ca^{2+}$ etc. are major constituents of seawater. Synthetic seawater was prepared based on Table 3 via using the density value of 1.029 g·cm$^{-3}$ of seawater and listed in Table 2. Varying $Ca^{+2}$ in synthetic seawater were realized via the addition of different amount of $CaCl_2$. Natural seawater sample (~100 ml) was collected by Mr. William McGee (Sandwich, Mass. 02563) and filtered by a WHATMAN® filter paper with a pore size of 2 μm before use. Similarly as in synthetic seawater, variations of $Ca^{+2}$ in natural seawater were achieved adding different amount of $CaCl_2$. For the study on the pH influence, synthetic seawater and natural seawater were adjusted to three typical pH values at 7.0, 8.0, and 8.5 by NaOH and HCl. For the interference study, synthetic seawater and natural seawater containing various $Mg^{+2}$ were prepared via adding different amount of $MgSO_4$ chemical.

TABLE 2

Preparation of synthetic seawater

| Salt | Molecular weight | Concentrations (millimole/liter, mM) |
|---|---|---|
| NaCl | 58.44 | 483 |
| KCl | 74.56 | 10.5 |
| $MgSO_4$ | 120.37 | 54.4 |
| $CaCl_2$ | 110.99 | 10.6 |

Adjust pH to 8.0 or other pH values by NaOH

TABLE 3

Major ions in sea water (Salinity = 35)*

| Ions | Concentrations (millimole/liter, mM)# |
|---|---|
| $Na^+$ | 481 |
| $K^+$ | 10.5 |
| $Mg^{2+}$ | 54.1 |
| $Ca^{2+}$ | 10.5 |
| $Cl^-$ | 55.9 |
| $SO_4^{2-}$ | 29.0 |

*http://en.wikipedia.org/wiki/Seawater.
Average density value of 1.025 g · cm$^{-3}$ is used for the mass-volume conversion of seawater.

The measurements were performed by Chronocoulometry using an electrochemical analyzer (for example, CH Instruments 720C). Measurements were carried out within a three-electrode electrochemical system, which was configured by connecting the fabricated sensor as the working electrode, using the silver (Ag) wire as the reference electrode, and with platinum (Pt) wire serving as the counter electrode. Chronocoulometry, which is a classical electrochemical technique, is the measurement of charge (coulombs) as a function of time (chrono). As a convenient, rapid and reliable technique, chronocoulometry has been extensively exploited for detection and determination of adsorbed species on electrode surface, including electrochemical active reactants (International Journal of Nanomedicine 7, 527 (2012), incorporated herein by reference) and electrochemical inert ions (Journal of Electroanalytical Chemistry 578, 273 (2005), incorporated herein by reference). The developed sensor herein is similar to the latter: the electrochemical inert species ($Ca^{+2}$) were specifically "adsorbed" onto the electrode surface by the immobilized chelating molecules (fluo-3), which instantaneously induced the changes of electrode charge. These electrode charge changes were recorded by chronocoulometry technology.

Although, in the above exemplary embodiment, chronocoulometry is used to perform the measurements, in embodiments in which the substrate is a conductor the measurement can also be performed by measurement of current, amperometric measurement, including the measurement of impedance.

Figure 3A:
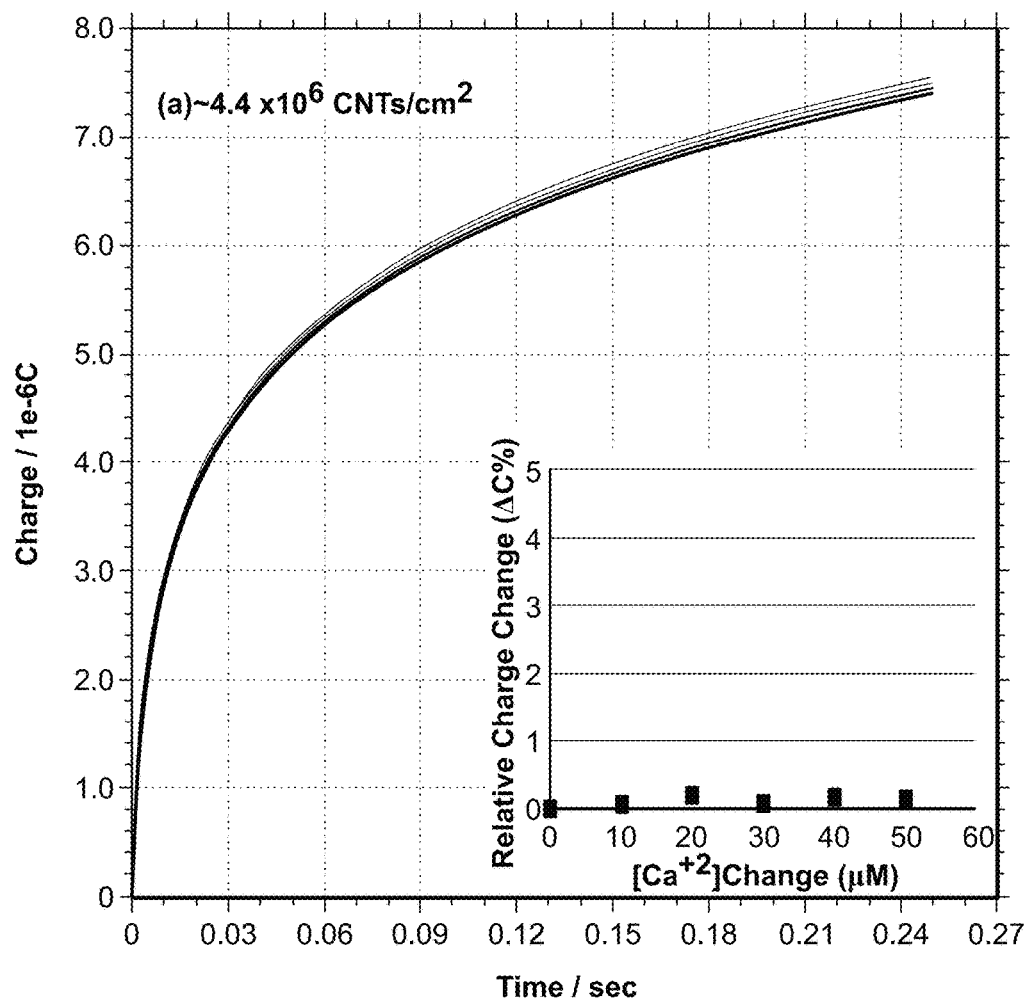
FIGS. 3a-c show results using one embodiment of the sensor of these teachings.
Figure 3B:
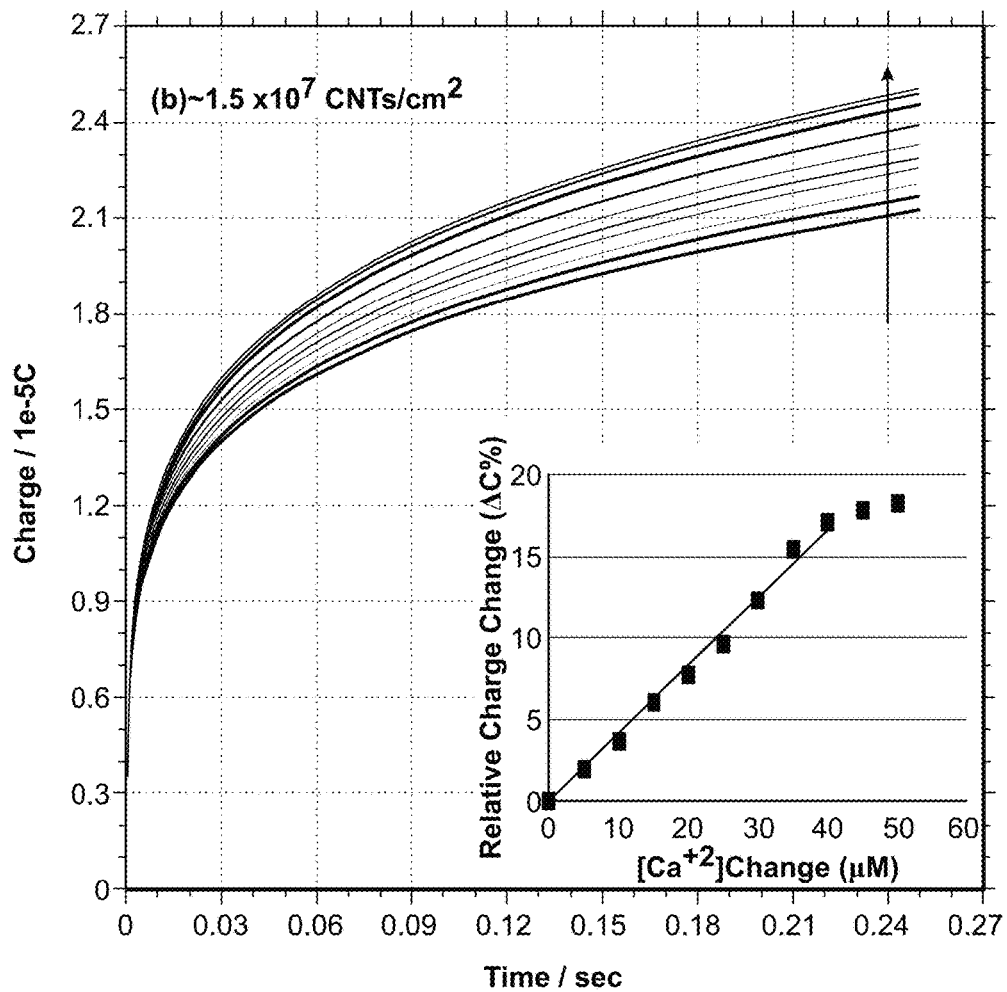
Figure 3C:
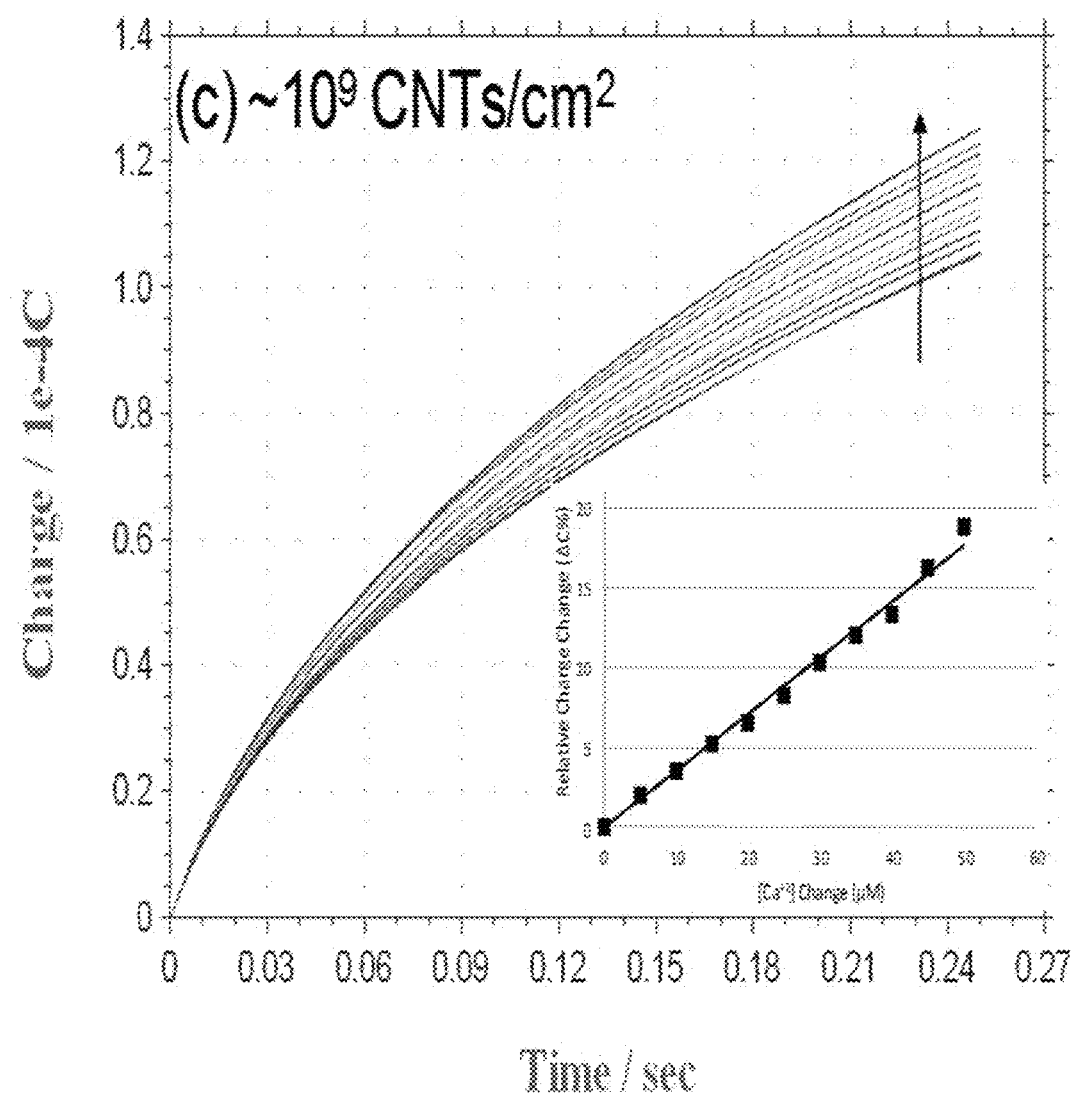

It is well known that ions of $Na^+$, $K^+$, $Mg^{2+}$ and $Ca^{2+}$ are major constituents of seawater and the detailed information is listed in Table 3. Synthetic seawater was prepared based on this formula and described in the experimental section (Table 2). It is also known that the density of seawater ranges from 1.020 to 1.029 g·cm$^{-3}$. To ensure the sensor's capability, the density value of 1.029 g·cm$^{-3}$ was used to calculate the molar of each ions and prepared the synthetic seawater. Consequently, the prepared synthetic seawater has a higher background and interference than natural seawater (Tables 2 and 3). In order to establish a suitable dynamic range, the influence of the packing density of MWCNT array on dynamic range was assessed. FIGS. 3a-3c show, in the exemplary embodiment where the measured ions are calcium ions, Chronocoulometric behaviors of three sensors with different packing densities of MWCNT array with (a) ~4.4×10$^6$; (b) ~1.5×10$^7$; (c) ~10$^9$ CNTs/cm$^2$ upon the successive addition of calcium ion up to 0.050 mM with intervals at 5 μM in synthetic seawater. The insets show plots of the relative electrode charge change (ΔC %) against the changes of $Ca^{+2}$ in synthetic seawater. The (ΔC %) is defined as the relevant electrode charge change (ΔC) divided by the electrode charge ($C_o$) in the starting solution (as-prepared synthetic seawater).

As shown in FIGS. 3a-3c, three sensors with distinct packing density were fabricated and assessed in synthetic seawater upon the successive addition of calcium ion up to 50 μm with an interval at 5 μM via chronocoulometric measurements. The corresponding plots of relative electrode charge change (ΔC %) with $Ca^{+2}$ change are illustrated in the insets. The extrapolation of relative electrode charge change (ΔC %) is determined as follows: First, the electrode charge in as-prepared synthetic seawater was measured and then utilized as the starting point ($C_o$). The charge change value (ΔC) was then obtained by subtracting the starting value ($C_o$) from the relevant electrode charge (C), followed by dividing the obtained charge change (ΔC) with the starting point ($C_o$). A negligible and random response from the sensor against $Ca^{+2}$ changes was observed for the sensor with a packing density at ~4.4×10$^6$ CNTs/cm$^2$ (FIG. 3a). This indicates that the sensor quickly saturated in synthetic seawater because of the presence of high background concentration of calcium ion (10.6 mM). By enhancing the density from ~4.4×10$^6$ (FIG. 3a) to ~1.5×10$^7$ CNTs/cm$^2$ (FIG. 3b), the signal of the sensor linearly changed against Ca$^{+2}$ changes up to 0.040 mM and reached a plateau afterwards; and with a density of ~10$^9$ CNTs/cm$^2$ (FIG. 3c), the linear response range is clearly beyond 50 μM of Ca$^{+2}$ change in synthetic seawater. This expanding behavior in the sensing range with the increasing packing density is, most probably, due to the enhanced loading density of fluo-3 within a more densely packed MWCNT array. With a suitable packing density (~10$^9$ CNTs/cm$^2$) of CNT array it is possible to ensure a proper dynamic range for determination of Ca$^{+2}$ changes in presence of high background Ca$^{+2}$ (~10.6 mM) and high interference (e.g. Mg$^{+2}$) (~54.4 mM).

Figure 4A:
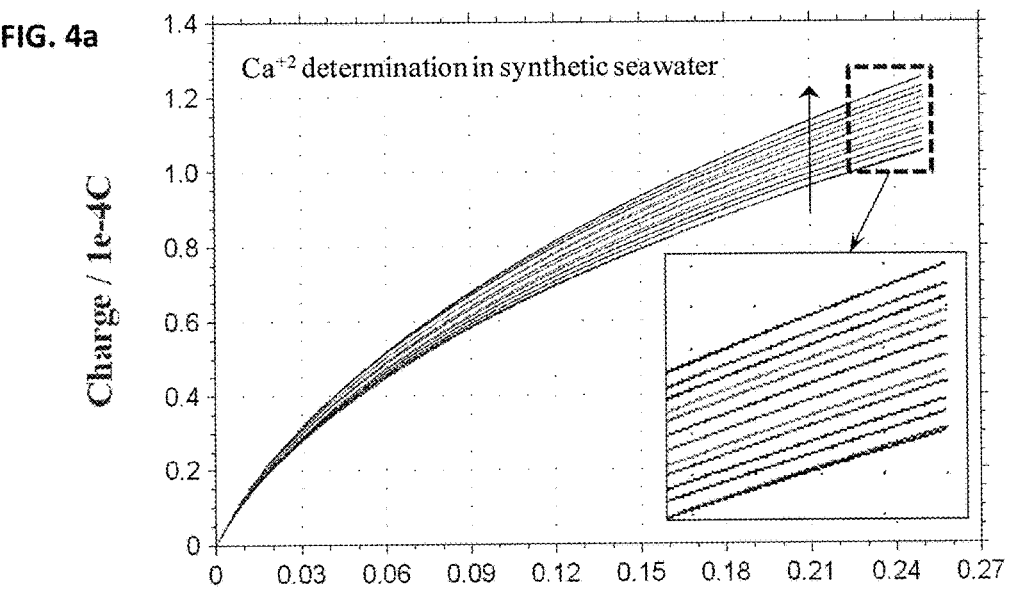
FIGS. 4a-7 represent more results obtained using one embodiment of the sensor of these teachings.
Figure 4B:
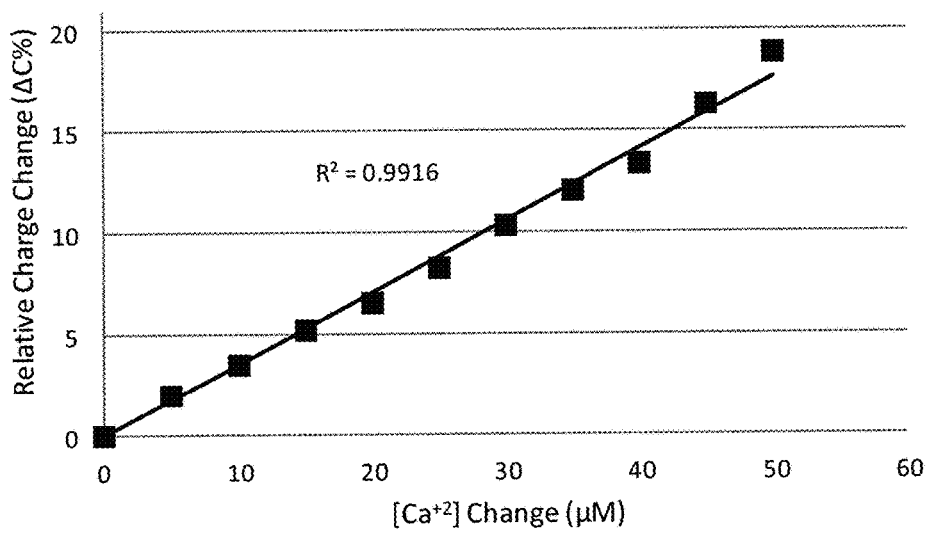

FIGS. 4a-4b show results of Chronocoulometric behaviors of the exemplary embodiment of the sensor. FIG. 4a shows Chronocoulometric behaviors of the sensor with the packing density of MWCNT array at ~10$^9$ CNTs/cm$^2$ upon the successive addition of 5 μM of calcium ion in synthetic seawater. The inset shows the zoomed-in area. FIG. 4 (b) shows a Plot of the relative electrode charge change (ΔC %) against the changes of Ca$^{+2}$ in synthetic seawater. The (ΔC %) is defined as the relevant electrode charge change (ΔC) divided by the electrode charge in the starting solution (as-prepared synthetic seawater).

The chronocoulometric curves of the sensor with the proper packing density against the various changes of Ca$^{+2}$ in synthetic seawater are represented in FIG. 4a and comprehensively analyzed in this section. The chronocoulometric determined electrode charge clearly shows its sensitive dependence on the small changes of Ca$^{+2}$ in presence of high background Ca$^{+2}$. As described in the above section, the relative electrode charge changes were calculated and plotted with the Ca$^{+2}$ changes. FIG. 4b shows the dependence of the calculated relative electrode change (ΔC %) on the changes of Ca$^{+2}$ in synthetic seawater. A good linear relationship are given between the relative charge change and the Ca$^{+2}$ change. This can be explained by that the specific capture of Ca$^{+2}$ by the immobilized fluo-3 molecules induces a higher permittivity and lower resistivity, leading to an increased capacitance and a decreased surface resistance. In addition, the synthetic seawater contains 10.6 mM of calcium ion, which is 0.4 mM higher than the concentration (~10.2 mM) in natural seawater, implying that the sensor is applicable to the determination of Ca$^{+2}$ change (~0.050 mM) in natural seawater. The ability of the sensor of these teachings to measure small Ca$^{+2}$ changes (50 μM) with a sensitivity of 5 μM has been demonstrated in synthetic seawater.

Figure 5A:
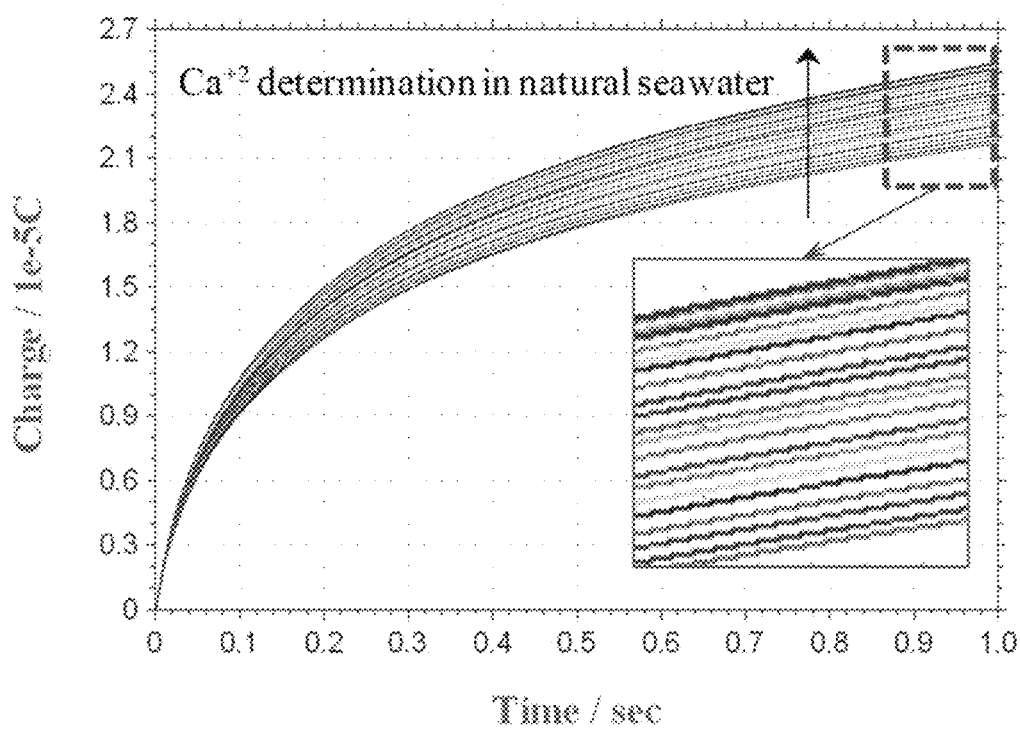
Figure 5B:
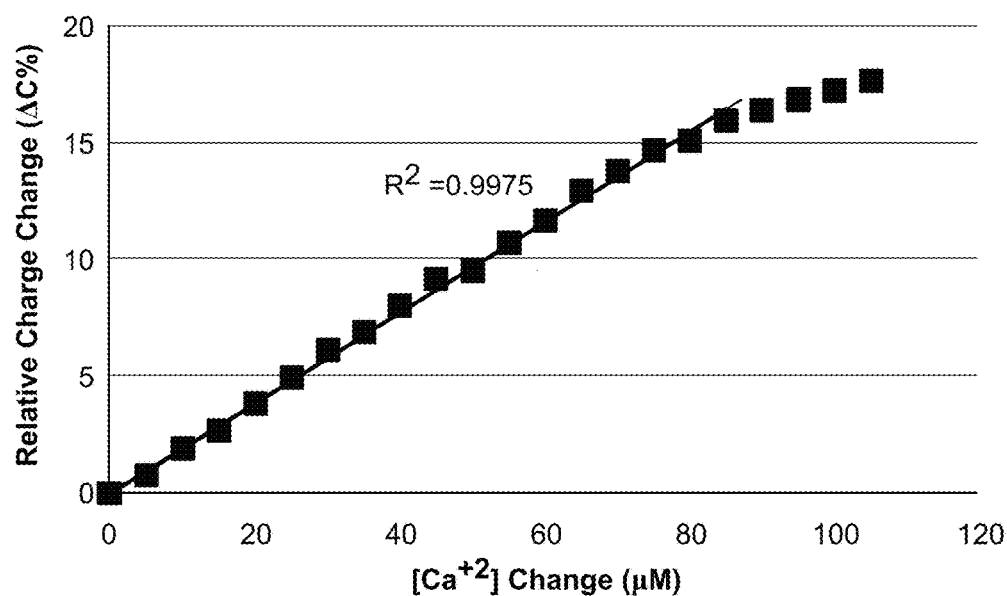

A sensor with the high precision performance requires both sensitivity and specificity. Therefore, one of the requirements is that the sensor should be selective and not affected by the presence of other ions like magnesium ion. As illustrated in FIG. 1c, a fluo-3 interacts with one calcium ion. The formed coordination complex can be described in terms of the set of four ligands each donating a pair of electrons to a metal centre (calcium ion). Because of the similarity (e.g. radius and charge) of magnesium and calcium ions and also because of the high concentration of magnesium ion in seawater (~54.1 mM), the magnesium ion is considered as a major interference for the detection of calcium ion. The sensor's selectivity in both synthetic and natural seawater has been measured by adding the major interfering ion —Mg$^{+2}$. FIGS. 5a, 5b show the chronocoulometric behaviors of a sensor against the addition of magnesium ion in both synthetic seawater (a) and natural seawater (b). As can be seen in FIG. 5a, the obtained chronocoulometric curves randomly and negligibly shifted with the addition of Mg$^{+2}$. If extrapolating those electrode charge changes into the relative change and comparing to the plots upon Ca$^{+2}$ (Inset in FIG. 5a), the difference are even more significant and clear. This is because Ca$^{+2}$ ions are much more strongly and selectively adsorbed on the electrode surface than the interfering ion (Mg$^{+2}$). Hence, the adsorption of Mg$^{+2}$ on the electrode surface can be neglected.

This is expected due to the unique property of fluo-3 molecule towards Ca$^{+2}$. It is well known that the fluo-3 molecule has a much higher affinity for Ca$^{+2}$ than for the main interfering ion (Mg$^{+2}$) in which log($K_{Ca}/K_{Mg}$)=5.2. Meanwhile, a layer of non-conducting polymer (polyphenol) was also coated onto the bare electrode surface to block the unspecific contact between other ions (e.g.Mg$^{+2}$) and bare electrode surface. The superior specificity of fluo-3 plus the non-conductive polymer coating allows tailoring and achieving a desirable precision for detection and determination of Ca$^{+2}$ change in seawater.

Figures 6A, 6B:
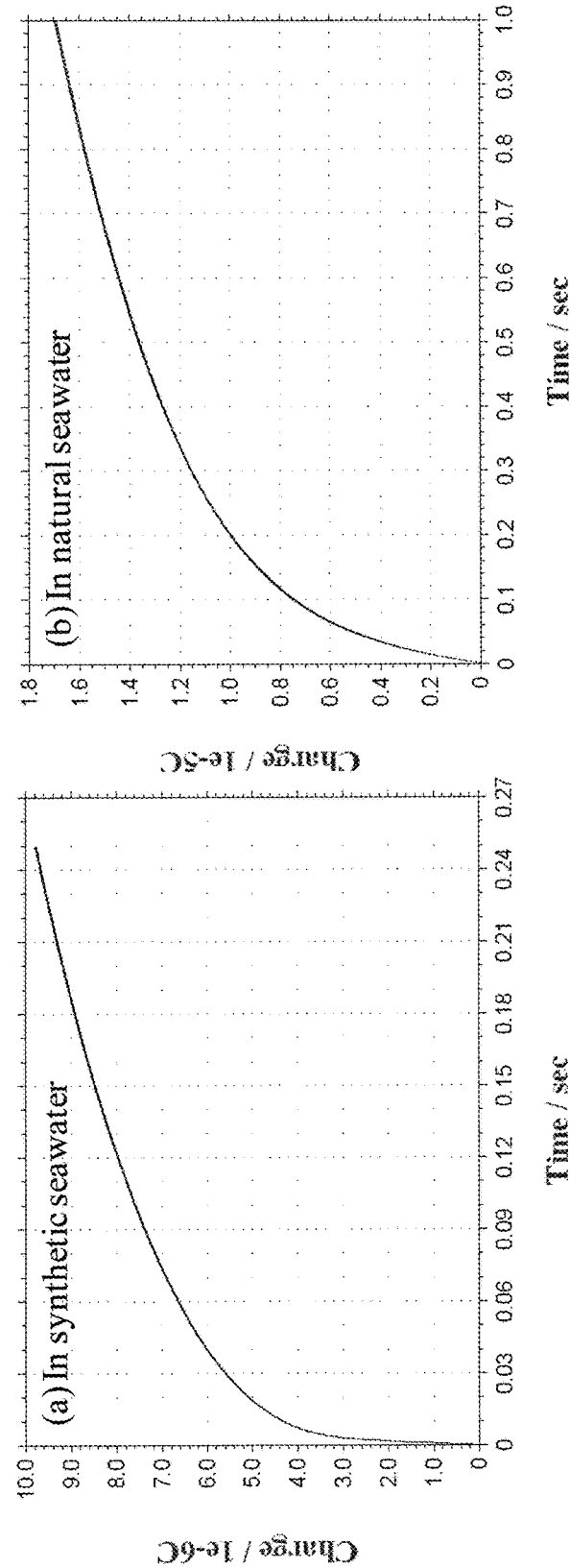

The pH of seawater is known to vary within a range of 7.4 to 8.4(Nature 437, 681 (2005), incorporated herein by reference). The effect of pH variation on the sensor therefore has to be considered. For this purpose, the fabricated sensor was tested in both synthetic and natural seawater in three pH values at 7.0, 8.0 and 8.5. This compares well with the pH variation (from 7.4 to 8.4) in natural seawater. FIG. 6a, 6b show Chronocoulometric behaviors of a sensor of these teachings upon three different pH values at 7.0, 8.0, and 8.5 (a) in synthetic seawater (b) in natural seawater, respectively. FIGS. 6a-6b show that there is no perceptible difference observed among the chronocoulometric curves against three different pH values in synthetic seawater (a) and natural seawater (b). Since on the electrode surface only the immobilized fluo-3 molecules can interact with ions, we believe that this pH-resistive performance of the sensor is related to the pKa possessed by the chelating molecule of fluo-3, which has a pKa value between 5.4 and 6.4 (fluo-4 has a similar pKa-about 5.6 so it is still insensitive to pH). Consequently, when pH of solution ranging from 7.0 to 8.5, the hydrogen ion is not expected to participate in the calcium ion complexation step of fluo-3. The sensor performance is not affected by pH variations in the dominant range seen in sea water.

Figure 7:
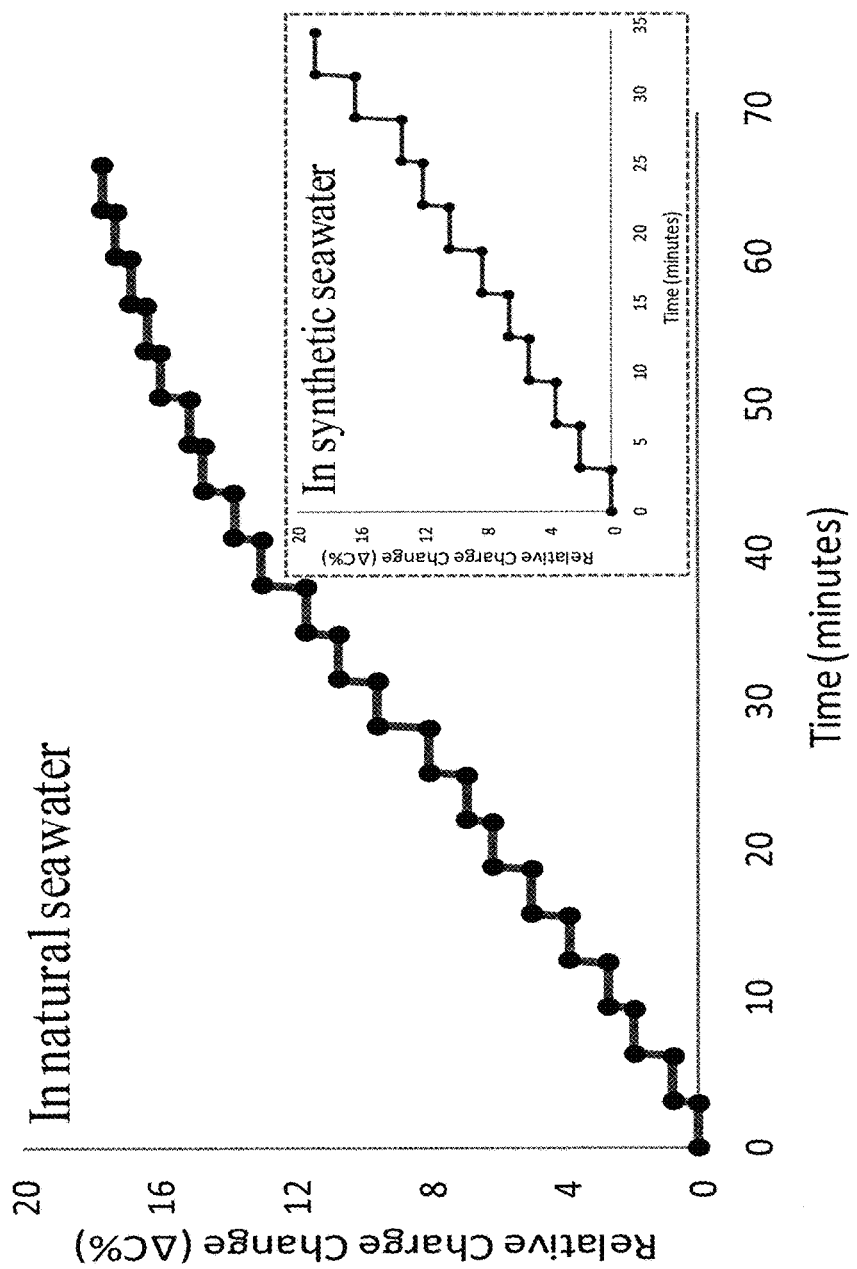

Because the sunlight is the dominant energy source at the earth's surface, and thus many species including reef corals are in response to solar photocycle (24-hour time scales), study of diel (24-hour) variations is important and has helped reveal which biogeochemical processes occur relatively rapidly in natural waters and therefore which processes play an integral and important role in the normal functioning of natural water systems (Chemical Geology 2011, 283, 3-17), incorporated herein by reference. However, because of the lack of a quick and sensitive method, the expense and inconvenience sampling or sophisticated instruments are always required for monitoring calcification rate. The detection method of these teachings is able to detect relatively small Ca$^{+2}$ changes (~0.050 mM) during the diel (24-hour) cycles. FIG. 7 shows that quick and sensitive detection of Ca$^{+2}$ changes in natural seawater upon the successive addition of 0.005 mM of calcium ion. The inset shows quick and sensitive response against Ca$^{+2}$ change in synthetic seawater. Each detection took around 3 minutes. FIG. 7 illustrates the change of relative electrode charge change (ΔC %) upon the successive addition of calcium ion (0.005 mM) with a time interval at ~3 minutes. As show in FIG. 8, the sensor of these teachings is able to quickly and sensitively determine each addition of 0.005 nM of calcium ion in natural seawater up to 0.085 mM and synthetic seawater (Inset in FIG. 7), respectively. The each detection time for every determination is slightly more than 3 minutes as presented in FIG. 7 and is mainly related to two steps: capture and measurement. After varying the $Ca^{+2}$ change (0.005 mM) in synthetic or natural seawater, a 3-minute quite time was given to ensure the sensing units sufficiently interact or capture $Ca^{+2}$ prior to each electrochemical measurement. Subsequently, chronocoulometric measurement was performed. The measurement time can be varied (user-defined), but within seconds.

As stated hereinabove, the quick detection is possibly due to the following reasons: rapid capture owing to high affinity of fluo-3 towards calcium ion, sensitive and immediate transduction of capture events, and fast chronocoulometric measurements. Considering the time scales of one diel cycle (24-hour), the detection method presented herein can quickly quantify $Ca^{+2}$ changes after one diel cycle in seawater.

Figure 8:
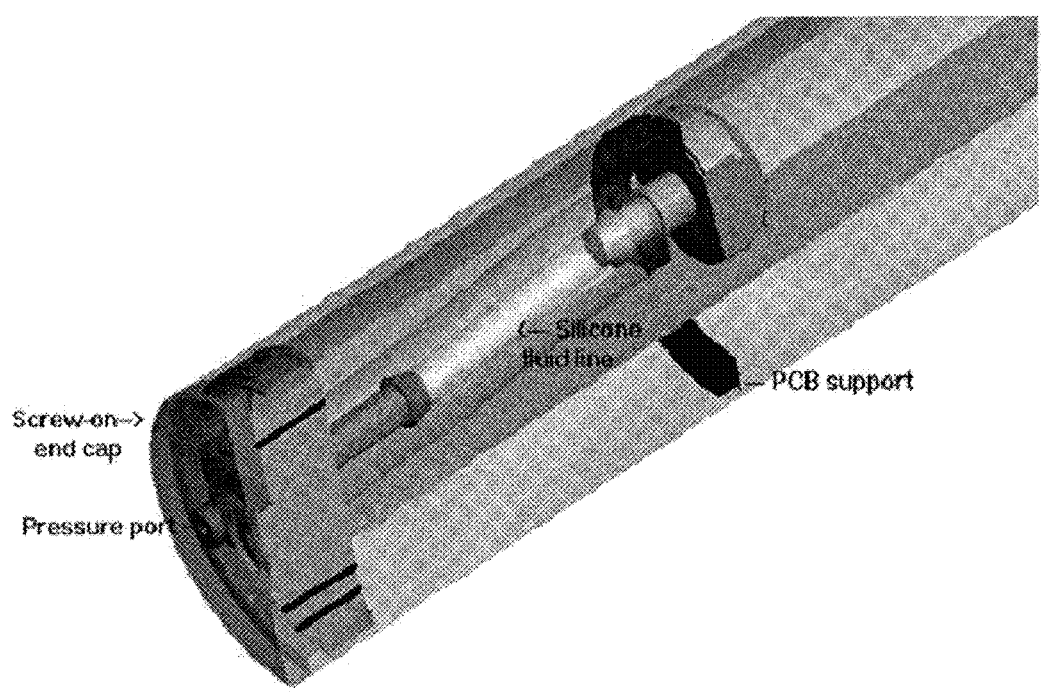
FIG. 8 shows a cutaway view of one embodiment of the sensor system.

A cutaway view of one embodiment of the sensor system is shown in FIG. 8. The enclosure of that embodiment is constructed from 6061 aluminum to survive deployment at a depth of 300 FSW. Young's modulus (Y), yield strength (E) and Poisson's ratio (v) were used to calculate the required ratio of wall thickness to diameter using Equations (1) and (2) with a safety margin of 30% submersion depth added to the result.

$$t/D_{yield}(press) = \frac{1}{2}\left(1 - \sqrt{1 - \frac{2*press}{Y}}\right) \quad (1)$$

$$t/D_{buckle}(press) = \left[press*\left(\frac{1-v^2}{2*E}\right)\right]^{\frac{1}{3}}. \quad (2)$$

A similar calculation was performed for the failure of the end cap which houses the sensor using the expression of Equation 3.

$$t/D_{endplate}(press) = \frac{1}{2}\sqrt{\frac{3\left(\frac{3}{v}+1\right)}{\frac{8}{v}}\frac{press}{Y}}. \quad (3)$$

The configuration of the window used to support the sensing unit also has to consider the effect of pressure. A simple O-ring seal serves as the sealing mechanism for the sensing window to allow easy replacement during service. The entire sensor module consisting of the sensor head at the end and the electronics on the inside of a housing.

Figure 9:
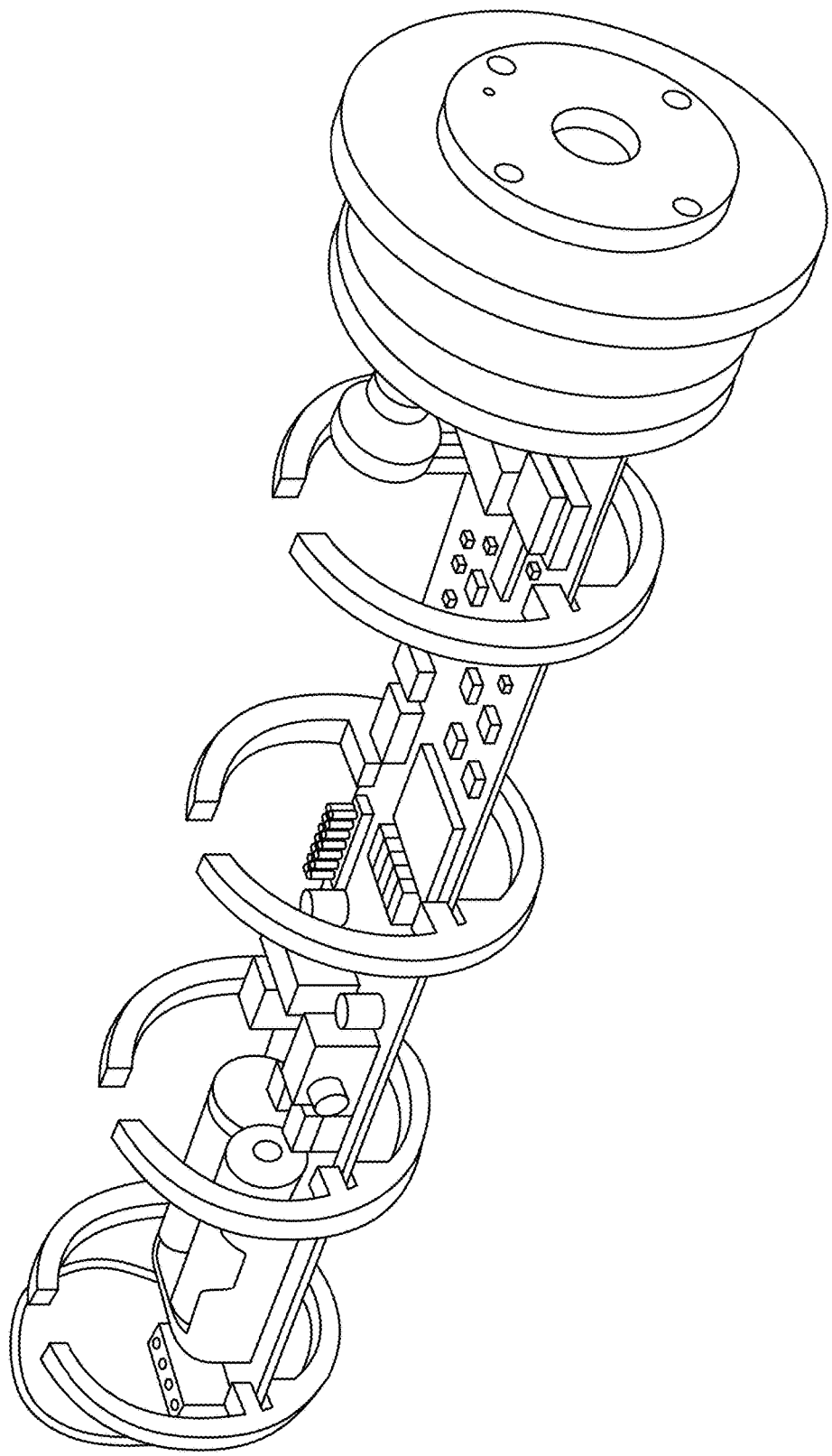
FIG. 9 shows a photograph of an embodiment of an integrated sensor module.

FIG. 9 shows a photograph of an embodiment of an integrated sensor module with electronics and sensor heads. The photo shows the brass plate and wire mesh of the sensing head attached to the end plate of the recorder. The unit's electronics are attached to the optical head mounted inside the end plate. The pressure sensor of the recorder is visible just behind the end plate and before the first of four white DELRIN® support rings that hold the board in place once inside the enclosure's tubular body. The black VITON® o-ring of the end plate forms a seal with the inside surface of the tubular body. The battery pack is carried at the back end of the unit in front of the blue terminal block used to connect the communication cable used to recover data during the field trials.

Characterization is performed by Chronocoulometry using an electrochemical analyzer (for example, but not limited to, CH Instruments 720C. These measurements are carried out within a three-electrode electrochemical system, which is configured by connecting the fabricated sensor as the working electrode, the silver (Ag) wire as the reference electrode, and platinum (Pt) wire serving as the counter electrode. The method involves the measurement of charge (coulombs) as a function of time (chrono). In the exemplary embodiment, a constant applied voltage of 200 mV was used (it should be noted that this is not a limitation of these teachings) and the change in charge, resulting from the change in calcium ion concentration, was measured as a current change. A miniaturized electronics measurement board (that will go into the sensor prototype as shown in FIG. 8) simulates the same function. A microcontroller can be used both for data collection and data processing.

Pressure & Temperature sensor: conventional pressure/temperature sensor module that can work up to pressures of 14 atmospheres (or 140 FSW) and temperatures −40 to +85° C. (such as, but not limited to, Measurement Specialties, Model MS5541C) can be used. In one instance, the features of the pressure sensor are:

It is a piezoresistive silicon sensor with 0-14 bar range with a resolution of 1.2 mbar
Very small (6 mm×6 mm)
16 bit ADC
Low voltage and low power consumption
3-wire serial interface
Already used in diving computer and diver watches
No external components required.

In one embodiment, the data evaluating the sensor perfoiinance at different pressures ranging from 15 to 150 PSI (which corresponds to 300 FSW) and at different temperatures ranging from about 2° C. to 25° C. is collected and then is used to program the electronic board for both pressure and temperature compensation. The new system electronics integrates temperature and pressure compensation. In one instance, the compensation is achieved by including a second programmable microprocessor that is coupled to the digital pressure or temperature sensor.

In one embodiment, the sensor system is able to survive deployment at a depth of 300 FSW in the ocean. This translates to a pressure range of 1-5 atmospheres and temperature range of 2°-25° C. (depending on the time of the year). The potential failure of the sensor can arise from three different aspects: 1) distortion of the substrate, a silicon wafer in one embodiment, 2) mechanical integrity of the CNTs and 3) Binding of the sensing element (chelating molecule) to CNTs.

Figure 10:
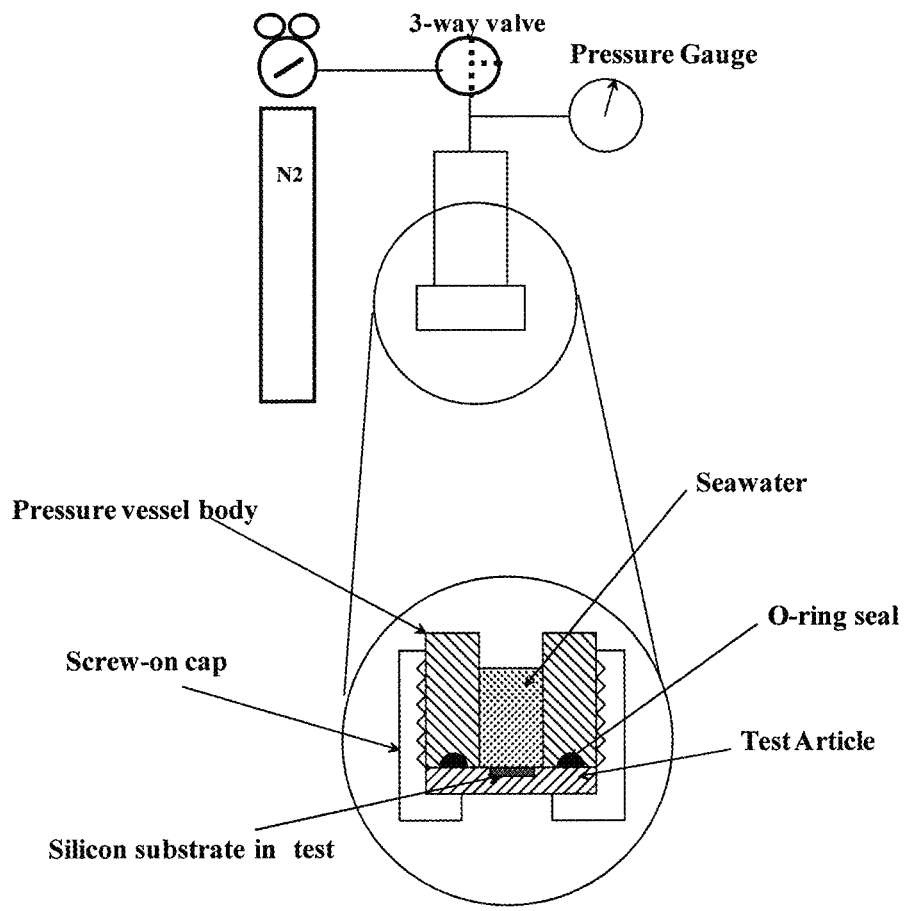
FIG. 10 shows a schematic representation of an apparatus for pressure testing a substrate as used in these teachings.

1. Silicon substrate: in one embodiment, Silicon substrate with a size of 1 cm×1 cm is used as the supporting substrate on which the CNT array will be grown and sensing materials will be deposited. Tests of the silicon substrate are conducted to determine susceptibility for failure under hydrostatic pressure. The test article is mounted in a test chamber which will be partially filled with seawater and pressure applied from a cylinder of compressed gas. Pressure within the vessel will be slowly increased while being monitored with an in-line pressure gauge. From the pressure tests, the silicon thickness is selected. The same method can be used to select the thickness of other embodiments of the substrate material. In one instance, tests are performed using the apparatus shown in FIG. 10.

2. CNTs: Considering that carbon nanotube is a hollow cylinder, the mechanical strength of carbon nanotube is considered under such pressure variations. The thickness (t)

to diameter (D) ratios have been calculated using the standard expressions for collapse pressures, Eqns. 4 and 4 below:

$$t/D_{yield}(\text{press}) = \frac{1}{2}\left(1 - \sqrt{1 - \frac{2*\text{press}}{Y}}\right) \quad \text{Eqn. 4}$$

$$t/D_{buckle}(\text{press}) = \left[\text{press} * \left(\frac{1-v^2}{2*E}\right)\right]^{\frac{1}{3}} \quad \text{Eqn 5}$$

Figure 11:
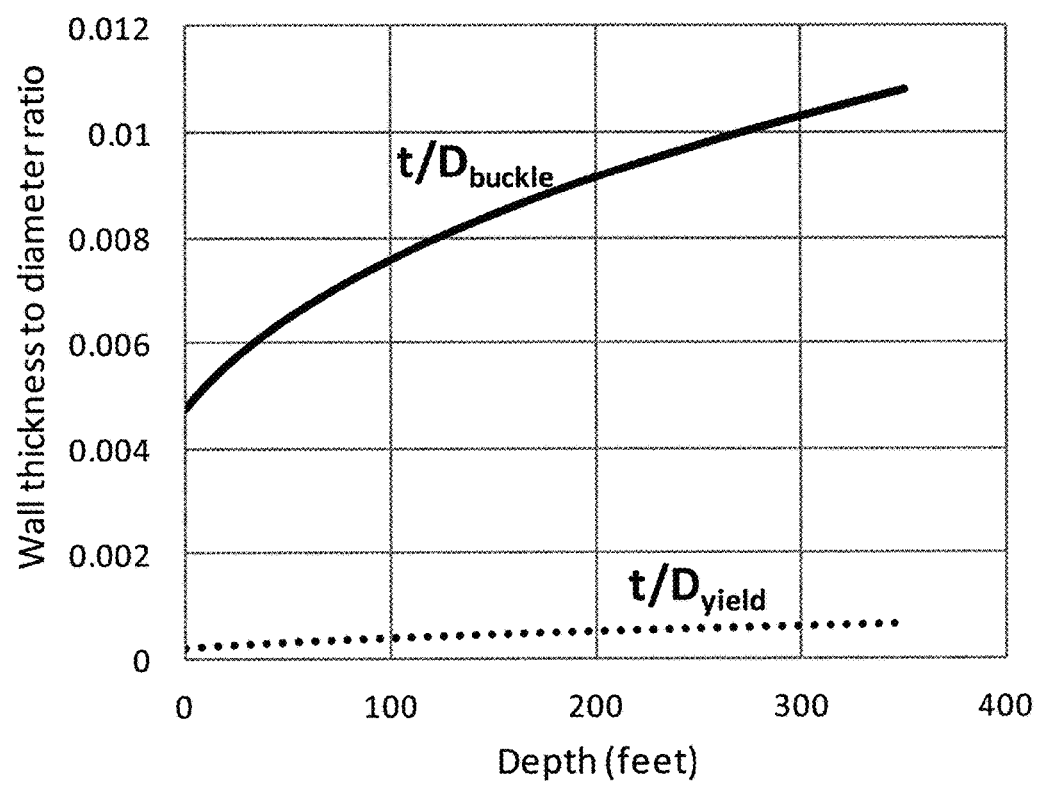
FIG. 11 is a graphical representation of wall thickness to diameter ratios versus submersion depth for yield and buckle failure of the multi-wall carbon nanotube.

Plots of the ratio versus submersion depth from calculations for carbon nanotube are shown in FIG. 11. Any ratio of nanotube wall thickness to diameter above the two lines of FIG. 11 will survive the submersion depth indicated in the graph.

Figure 12:
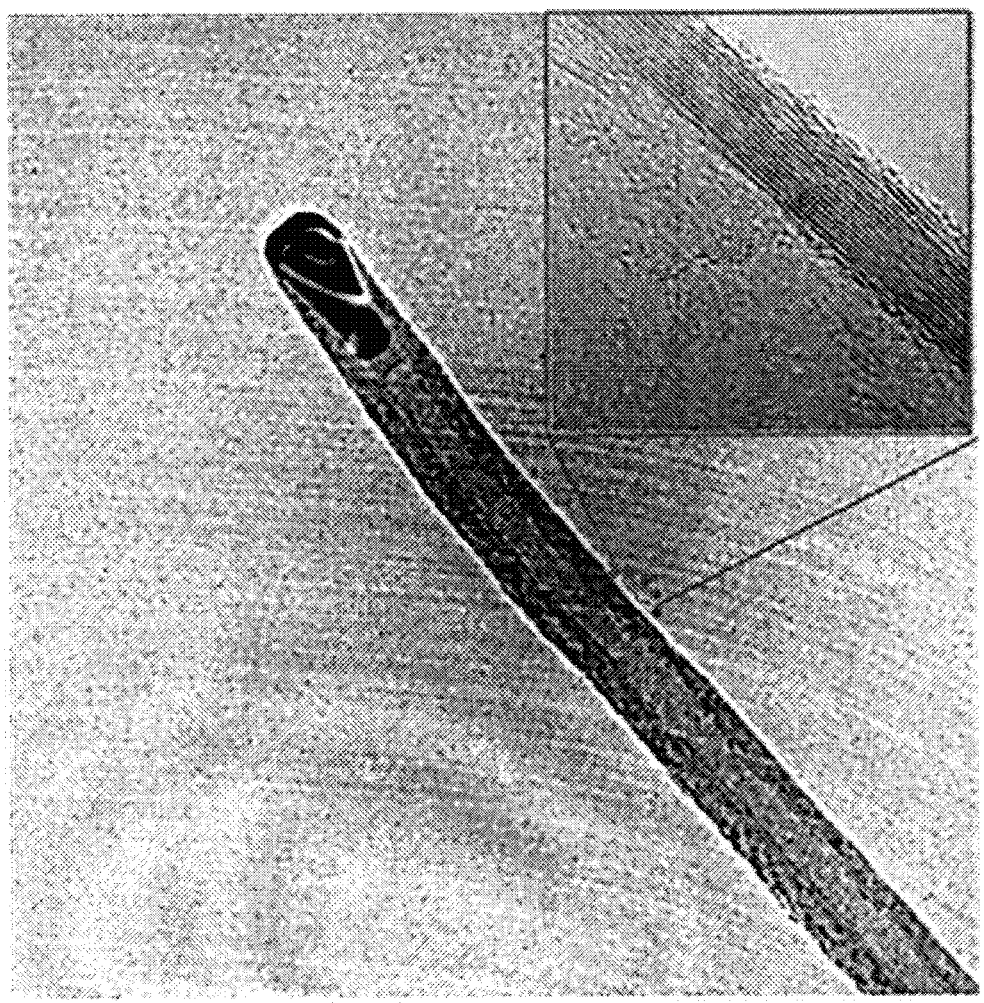
FIG. 12 shows a structure of multi-wall carbon nanotube as used in these teachings.

The Young's modulus and tensile strength of the nanotube are obtained from published papers. Professor C. Lieber (Harvard University) and his co-workers have reported the Young's modulus (Y) of the nanotube to be 1.28±0.5 TPa with no dependence on tube diameter for MWNT while the Poisson ratio v=0.19 and the Tensile strength (E) of 45 GPa are utilized for the calculation. Compression strength is another important mechanical parameter, but its nature is completely different from the strength in tension. Usually it does not involve any bond reorganization in the atomic lattice, but is due to the buckling on the surface of the outermost layer of nanotube. The multi-walled CNT arrays are fabricated, in one instance, using the plasma enhanced chemical vapor deposition (PECVD) method. Such MCNTs have multilayer graphitic sidewalls (~15 walls) and hollow core (FIG. 12). Considering the average diameter of the nanotube at 100 nm, the wall thickness to diameter is more than 0.05, which is far above the two lines in FIG. 11. These calculated values indicate that multiwalled carbon nanotube array can withstand the pressure corresponding to ocean depth of 300 FSW.

3. Stability of the sensor molecule Fluo-3: The dissociation constant under pressure of the chelating sensor molecule is given by: K(p)=K(o) exp (pΔV/RT), where, K(o) refers to the dissociation constant under atmospheric pressure. Since ΔV is practically zero in the present application, the dissociation constant of fluo-3 towards calcium ion is substantially temperature and pressure-independent.

It should be noted that, although exemplary embodiments have been presented, these teachings are not limited only to those exemplary embodiments.

For the purposes of describing and defining the present teachings, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Although the invention has been described with respect to various embodiments, it should be realized these teachings are also capable of a wide variety of further and other embodiments within the spirit and scope of these teachings.

What is claimed is:

1. A system comprising:
a substrate;
a plurality of multi-walled carbon nanotubes, each multi-wailed carbon nanotube from the plurality of multi-walled carbon nanotubes having two ends and a surface extending between the two ends;
one of the two ends being disposed on and operatively attached to the substrate, the other of the two ends not being disposed on the substrate;
a number of organic molecules bound to an external surface of at least one multi-walled carbon nanotube, each organic molecule having an end group configured to chelate a predetermined ion; and
a nonconducting polymer deposited on at least one portion of the external surface of each multiwalled carbon nanotube, the at least one portion not including locations on each multiwalled carbon nanotube at which an organic molecule is bound; the nonconducting polymer coating the at least one portion of the external surface, the external surface being a surface on which the number of organic molecules having an end group configured to chelate a predetermined ion are bound, and not coating the locations at which the number of organic molecules are bound; the number of organic molecules having an end group configured to chelate a predetermined ion not being bound to the nonconducting polymer; predetermined ion measurements being performed, after the predetermined ions bind to the organic molecules, by one of coulometric measurements or amperometric measurements.

2. The system of claim 1 wherein the predetermined ion is a calcium ion ($Ca^{2+}$); and wherein the end group is configured to chelate the calcium ion ($Ca^{2+}$).

3. The system of claim 2 further comprising an electrochemical analyzer configured to perform chronocoulometry.

4. The system of claim 2 wherein said each organic molecule is Fluo-3 ($C_{51}H_{50}Cl_2N_2O_{23}$-([2-(2-{2-[Bis(carboxymethyl)amino]-5-(2,7-dichloro-6-hydroxy-3-oxo-3H-xanthen-9-yl)phenoxy}ethoxy)-4-methylphenyl](carboxymethyl)amino}acetic acid).

5. The system of claim 2 wherein said each organic molecule binds to said one multi-walled carbon nanotube by a π-π interaction.

6. The system of claim 1 wherein the predetermined ion is a magnesium ion ($Mg^{2+}$); and wherein the end group is configured to chelate the magnesium ion ($Mg^{2+}$).

7. The system of claim 6 wherein said each organic molecule is Mag-Fluo-4 ($C_{25}H_{13}F_2K_4NO_{10}$).

8. The system of claim 6 wherein said each organic molecule binds to said one multi-walled carbon nanotube by a π-π interaction.

9. The system of claim 6 further comprises an electrochemical analyzer configured to perform chronocoulometry.

10. The system of claim 1 wherein the predetermined ion is a Zinc ion ($Zn^{2+}$); and wherein the end group is configured to chelate the Zinc ion ($Zn^{2+}$).

11. The system of claim 10 wherein said each organic molecule is $C_{24}H_{24}F_2K_4N_2O_{12}$-N-(carboxymethyl)-N-[4-(2,7-difluoro-6-hydroxy-3-oxo-3H-xanthen-9-yl)-2-methoxyphenyl].

12. The system of claim 11 wherein said each organic molecule binds to said one multi-walled carbon nanotube by a π-π interaction.

13. The system of claim 10 further comprises an electrochemical analyzer configured to perform chronocoulometry.

14. The system of claim 1 wherein the predetermined ion is a copper ion ($Cu^{2+}$); and wherein the end group is configured to chelate the copper ion ($Cu^{2+}$).

15. The system of claim 14 wherein said each organic molecule is glycyl-glycyl-histidine ($C_{10}H_{15}N_5O_4$).

16. The system of claim 14 wherein said each organic molecule binds to said one multi-walled carbon nanotube by forming amide bonds.

17. The system of claim 1 wherein said each multi-walled carbon nanotube is substantially perpendicular to said substrate.

18. The system of claim 1 wherein said substrate is selected from one of metal, glass or silicon.

19. The system of claim 1 wherein said nonconducting polymer is a polymer from the polyphenol class.

* * * * *